(12) United States Patent
Guo et al.

(10) Patent No.: US 12,310,792 B2
(45) Date of Patent: May 27, 2025

(54) ULTRASOUND-GUIDED DRUG-LOADED MICROBUBBLE DELIVERY METHOD AND ELECTRONIC DEVICE

(71) Applicant: Nanjing Leapsonics Technology Co., Ltd., Jiang Bei Xin Qu District (CN)

(72) Inventors: Wenyu Guo, Nanjing (CN); Jian An, Nanjing (CN); Feihong Dong, Nanjing (CN); Shuo Huang, Nanjing (CN); Jue Zhang, Nanjing (CN)

(73) Assignee: Nanjing Leapsonics Technology Co., Ltd., Nanjing (CN)

( * ) Notice: Subject to any disclaimer, the term of this patent is extended or adjusted under 35 U.S.C. 154(b) by 410 days.

(21) Appl. No.: 17/837,887

(22) Filed: Jun. 10, 2022

(65) Prior Publication Data

US 2022/0296215 A1    Sep. 22, 2022

Related U.S. Application Data

(63) Continuation of application No. PCT/CN2021/078155, filed on Feb. 26, 2021.

(30) Foreign Application Priority Data

Jun. 24, 2020  (CN) .......................... 202010588228.2

(51) Int. Cl.
*A61B 8/08*   (2006.01)
*A61B 8/00*   (2006.01)
(Continued)

(52) U.S. Cl.
CPC ................ *A61B 8/481* (2013.01); *A61B 8/06* (2013.01); *A61B 8/0891* (2013.01); *A61M 37/0092* (2013.01)

(58) Field of Classification Search
CPC ......... A61B 8/481; A61B 8/06; A61B 8/0891; A61B 8/483; A61B 8/488;
(Continued)

(56) References Cited

U.S. PATENT DOCUMENTS 6,475,148 B1    11/2002  Jackson et al.
6,740,039 B1 *  5/2004   Rafter ...................... A61N 7/00
                                                    601/2
(Continued)

FOREIGN PATENT DOCUMENTS

CN    101642607 A    2/2010
CN    102113898 A    7/2011
(Continued)

OTHER PUBLICATIONS

Extended European Search Report issued in counterpart European Patent Application No. 21828296.0, dated Jun. 5, 2023.
(Continued)

*Primary Examiner* — Anne M Kozak
*Assistant Examiner* — Kaitlyn E Sebastian
(74) *Attorney, Agent, or Firm* — Westbridge IP LLC

(57) ABSTRACT

A method of delivery of an ultrasound-guided drug-loaded microbubble, an electronic device, and a computer-readable storage medium are provided. The method includes: emitting a first ultrasonic signal by utilizing an array transducer, to break a drug-loaded microbubble in a current breaking region; emitting a second ultrasonic signal by utilizing the array transducer, to obtain an ultrasound image; identifying a contour of a blood vessel of the breaking region based on the ultrasound image; and updating a characteristic parameter of the breaking region based on the contour of the blood vessel. According to the method, the breaking region is updated in real time based on the contour of the blood vessel,
(Continued)

so that delivery accuracy of a drug-loaded microbubble is improved, and avoiding unnecessary tissue damage.

19 Claims, 7 Drawing Sheets

(51) Int. Cl.
*A61B 8/06* (2006.01)
*A61M 37/00* (2006.01)

(58) Field of Classification Search
CPC .......... A61B 2034/105; A61B 8/0833; A61M 37/0092; A61K 41/0028; A61N 7/00; A61N 2007/0039; A61N 2007/0052; A61N 2007/0095; A61N 2007/027
See application file for complete search history.

(56) References Cited

U.S. PATENT DOCUMENTS

| | | | |
|---|---|---|---|
| 2002/0151792 A1* | 10/2002 | Conston | A61B 8/481 600/439 |
| 2005/0084538 A1 | 4/2005 | Dayton et al. | |
| 2013/0046179 A1 | 2/2013 | Humayun | |
| 2014/0334706 A1* | 11/2014 | Toma | G16H 50/30 600/440 |
| 2015/0025373 A1* | 1/2015 | Kim | A61B 8/4416 600/431 |
| 2015/0105658 A1* | 4/2015 | Park | A61B 8/481 600/431 |
| 2018/0000441 A1* | 1/2018 | Wang | G06V 10/755 |
| 2019/0184204 A1* | 6/2019 | Ramamurthy | A61B 8/4461 |
| 2019/0329075 A1* | 10/2019 | Sutton | A61B 5/0036 |
| 2020/0077982 A1* | 3/2020 | Duncan | A61B 8/06 |

FOREIGN PATENT DOCUMENTS

| | | |
|---|---|---|
| CN | 103654842 A | 3/2014 |
| CN | 110022860 A | 7/2019 |
| CN | 110339494 A | 10/2019 |
| CN | 111729188 A | 10/2020 |
| WO | 2012030675 A1 | 3/2012 |
| WO | 2012083532 A1 | 6/2012 |

OTHER PUBLICATIONS

First Office Action issued in counterpart Chinese Patent Application No. 202010588228.2, dated Nov. 10, 2021.
International Search Report issued in corresponding PCT Application No. PCT/CN2021/078155, dated May 28, 2021.

* cited by examiner

ULTRASOUND-GUIDED DRUG-LOADED MICROBUBBLE DELIVERY METHOD AND ELECTRONIC DEVICE

CROSS-REFERENCE TO RELATED APPLICATIONS

The present application is a continuation application of International Application No. PCT/CN2021/078155 filed on Feb. 26, 2021, which claims priority to Chinese Patent Application No. 202010588228.2 filed on Jun. 24, 2020. Both applications are incorporated herein by reference in their entireties.

TECHNICAL FIELD

The present application relates to the field of ultrasonic technologies, and more particular, to a method of delivery of an ultrasound-guided drug-loaded microbubble, an electronic device, and a computer-readable storage medium.

BACKGROUND

A drug release system is a system that achieves a release of drugs through slow degradation of a carrier in the body or exogenous stimulation and induction after the drugs are encapsulated into the carrier and implanted or injected into the body, to increase drug concentrations of local lesion tissues.

In recent years, emergence of an ultrasound-targeted microbubble destruction (UTMD) technology has overcome two major challenging difficulties: targeted delivery of drugs and penetration of drugs into cells through blood vessels, and has drawn more and more attention. In the UTMD technology, an ultrasound contrast agent is utilized to induce a local part to generate a microflow and a shear force under a focused ultrasound action, which stimulates channels between pores of endothelial cell membranes and cells to be opened, thereby improving permeability of blood vessels and cell membranes, and facilitating targeted delivery of therapeutic drugs into cells.

At present, there are two kinds of main guidance methods for the UTMD technology: one is magnetic resonance imaging (MRI) guidance, and the other is ultrasound imaging guidance. An MRI-guided UTMD system generally performs monitoring by utilizing a magnetic resonance thermometry method, with a temperature accuracy of 1° C., a spatial resolution of 1 mm, and a temporal resolution of 1 s, but the equipment is expensive, and the operation is complicated. Although ultrasound imaging guidance overcomes a problem of high costs of MRI guidance, it requires a doctor's operation in processes of imaging monitoring and drug-loaded microbubble breaking, a delivery effect of a drug-loaded microbubble is affected by human factors, which makes delivery location of the drug-loaded microbubble inaccurate and spends a relative long time. It can be learned that how to analyze a monitoring image of imaging in real time to update a parameter of a breaking region located when a drug-loaded microbubble is broken and the like to implement automatic delivery of the drug-loaded microbubble and improve delivery accuracy and efficiency of the drug-loaded microbubble is an important problem that needs to be resolved urgently today.

SUMMARY

To resolve the foregoing problems in the prior art, embodiments of the present application provide a method of delivery of an ultrasound-guided drug-loaded microbubble and apparatus, an electronic device, and a computer-readable storage medium.

According to an aspect of the embodiments of the present application, a method of delivery of an ultrasound-guided drug-loaded microbubble is provided, including: emitting a first ultrasonic signal by utilizing an array transducer, to break a drug-loaded microbubble in a current breaking region; emitting a second ultrasonic signal by utilizing the array transducer, to obtain an ultrasound image; identifying a contour of a blood vessel of the breaking region based on the ultrasound image; and updating a characteristic parameter of the breaking region based on the contour of the blood vessel.

In an embodiment of the present application, after the identifying a contour of a blood vessel of the breaking region based on the ultrasound image, the method further includes: adjusting locations and shapes of a plurality of regions of interest of the breaking region based on the contour of the blood vessel; obtaining evaluation data of concentrations of drug-loaded microbubbles in the plurality of regions of interest based on the locations and shapes of the plurality of regions of interest; and adjusting, based on the evaluation data of the concentrations of drug-loaded microbubbles, an ultrasonic voltage used when the array transducer emits the first ultrasonic signal.

In an embodiment of the present application, the plurality of regions of interest include an upstream region of interest and a downstream region of interest, and the adjusting locations and shapes of a plurality of regions of interest of the breaking region based on the contour of the blood vessel includes: dividing the contour of the blood vessel of the breaking region into the upstream region of interest and the downstream region of interest by taking a center line of the breaking region as a dividing line, to learn locations and shapes of the upstream region of interest and the downstream region of interest.

In an embodiment of the present application, the adjusting, based on the evaluation data of the concentrations of drug-loaded microbubbles, an ultrasonic voltage used when the array transducer emits the first ultrasonic signal includes: increasing, based on average gray-scale values of the upstream region of interest and the downstream region of interest, the ultrasonic voltage used when the array transducer emits the first ultrasonic signal.

In an embodiment of the present application, the increasing, based on average gray-scale values of the upstream region of interest and the downstream region of interest, the ultrasonic voltage used when the array transducer emits the first ultrasonic signal includes: when a ratio of an absolute value of a difference between the average gray-scale values of the upstream region of interest and the downstream region of interest to the average gray-scale value of the upstream region of interest is greater than a drug-loaded microbubble breaking threshold, increasing the ultrasonic voltage used when the array transducer emits the first ultrasonic signal.

In an embodiment of the present application, the identifying a contour of a blood vessel of the breaking region based on the ultrasound image includes: inputting the ultrasound image into a target tracking model, to obtain the contour of the blood vessel, output by the target tracking model, of the breaking region.

In an embodiment of the present application, the inputting the ultrasound image into a target tracking model, to obtain the contour of the blood vessel, output by the target tracking model, of the breaking region includes: superposing a current ultrasound image and a previous ultrasound image to construct an ultrasound image sequence, and inputting the ultrasound image sequence into the target tracking model, to obtain the contour of the blood vessel, output by the target tracking model, of the breaking region.

In an embodiment of the present application, the updating a characteristic parameter of the breaking region based on the contour of the blood vessel includes: updating a size and a location of the breaking region based on the contour of the blood vessel.

In an embodiment of the present application, the method includes: determining a preselected breaking region as the current breaking region when the array transducer emits the second ultrasonic signal for the first time.

In an embodiment of the present application, the determining a preselected breaking region as the current breaking region when the array transducer emits the second ultrasonic signal for the first time includes: obtaining the ultrasound image when the array transducer emits the second ultrasonic signal for the first time, and selecting the breaking region based on a lesion region in the ultrasound image.

In an embodiment of the present application, the selecting the breaking region based on a lesion region in the ultrasound image includes: when the lesion region is a tumor lesion region or a cardiovascular lesion region, determining an upstream region of the lesion region as the breaking region that is selected based on the lesion region in the ultrasound image; and when the lesion region is a non-tumor lesion region or a non-cardiovascular lesion region, determining the lesion region as the breaking region that is selected based on the lesion region in the ultrasound image.

In an embodiment of the present application, the method further includes: ending delivery of current drug-loaded microbubble when a ratio of an absolute value of a difference between average gray-scale values of a current upstream region of interest and an initial upstream region of interest to the average gray-scale value of the initial upstream region of interest is less than a preset value, wherein the average gray-scale value of the initial upstream region of interest is obtained when the array transducer emits the second ultrasonic signal for the first time for obtaining the ultrasound image.

In an embodiment of the present application, the array transducer emits the first ultrasonic signal or the second ultrasonic signal under a signal sending condition that a mechanical index is less than 1.0 or 1.5.

According to another aspect of the present application, an apparatus for delivery of an ultrasound-guided drug-loaded microbubble is provided, including: a delivery module, configured to emit a first ultrasonic signal by utilizing an array transducer, to break a drug-loaded microbubble in a current breaking region; an imaging module, configured to emit a second ultrasonic signal by utilizing the array transducer, to obtain an ultrasound image; an identification module, configured to identify a contour of a blood vessel of the breaking region based on the ultrasound image; and a first parameter adjustment module, configured to update a characteristic parameter of the breaking region based on the contour of the blood vessel.

In an embodiment of the present application, the apparatus further includes: a second parameter adjustment module, configured to adjust locations and shapes of a plurality of regions of interest of the breaking region based on the contour of the blood vessel; an evaluation module, configured to obtain evaluation data of concentrations of drug-loaded microbubbles in the plurality of regions of interest based on the locations and shapes of the plurality of regions of interest; and a voltage adjustment module, configured to adjust, based on the evaluation data of the concentrations of drug-loaded microbubbles, an ultrasonic voltage used when the array transducer emits the first ultrasonic signal.

In an embodiment of the present application, the plurality of regions of interest include an upstream region of interest and a downstream region of interest; and the second parameter adjustment module is further configured to: divide the contour of the blood vessel of the breaking region into the upstream region of interest and the downstream region of interest by taking a center line of the breaking region as a dividing line, to learn locations and shapes of the upstream region of interest and the downstream region of interest.

In an embodiment of the present application, the voltage adjustment module is further configured to: increase, based on average gray-scale values of the upstream region of interest and the downstream region of interest, the ultrasonic voltage used when the array transducer emits the first ultrasonic signal.

In an embodiment of the present application, the voltage adjustment module is further configured to: when a ratio of an absolute value of a difference between the average gray-scale values of the upstream region of interest and the downstream region of interest to the average gray-scale value of the upstream region of interest is greater than a drug-loaded microbubble breaking threshold, increase the ultrasonic voltage used when the array transducer emits the first ultrasonic signal.

In an embodiment of the present application, the identification module is further configured to: input the ultrasound image into a target tracking model, to obtain the contour of the blood vessel, output by the target tracking model, of the breaking region.

In an embodiment of the present application, the identification module is further configured to: superpose a current ultrasound image and a previous ultrasound image to construct an ultrasound image sequence, and input the ultrasound image sequence into the target tracking model, to obtain the contour of the blood vessel, output by the target tracking model, of the breaking region.

In an embodiment of the present application, the first parameter adjustment module is further configured to: update a size and a location of the breaking region based on the contour of the blood vessel.

According to another aspect of the present application, a computer-readable storage medium is provided, where the storage medium stores a computer program, and the computer program is used to perform the method of delivery of an ultrasound-guided drug-loaded microbubble according to any one of the foregoing aspects.

According to another aspect of the present application, an electronic device is provided, including: a processor; and a memory, where the memory is configured to store instructions executable by the processor, and when the processor executes the instructions, the method of delivery of an ultrasound-guided drug-loaded microbubble according to any one of the foregoing aspects is implemented.

It can be learned that, according to the method of delivery of an ultrasound-guided drug-loaded microbubble and apparatus thereof, the electronic device, and the computer-readable storage medium provided in the embodiments of the present application, an ultrasonic signal is transmitted toward a drug-loaded microbubble in a current breaking region by utilizing an array transducer to break the drug-loaded microbubble, then ultrasound imaging is implemented by using the array transducer to obtain an ultrasound image, a contour of a blood vessel of the breaking region is obtained based on the ultrasound image, and a characteristic parameter of the breaking region is updated based on the contour of the blood vessel, to complete delivery of a drug-loaded microbubble of one period. Since a contour and a shape of a blood vessel constantly change, a parameter of a breaking region is updated in real time to adjust the breaking region, so that the contour of the blood vessel may still be accurately identified under changes of the contour of the blood vessel, thereby improving delivery accuracy of a drug-loaded microbubble, and making a delivery effect of the drug-loaded microbubble better. In addition, the parameter of the breaking region is constantly updated, so that the breaking region is always kept in the blood vessel, thereby avoiding unnecessary tissue damage caused when an ultrasonic signal is transmitted toward a tissue around the blood vessel, and further shortening a delivery time of the drug-loaded microbubble.

It should be understood that the description of the foregoing technical effects is merely exemplary and illustrative, and does not constitute any limitation on the present application.

BRIEF DESCRIPTION OF THE DRAWINGS

To make the objectives, technical solutions and advantages of the embodiments of the present application more explicit, the following further describes the embodiments of the present application in detail with reference to the accompanying drawings. It should be understood that the accompanying drawings constitute part of this specification. The accompanying drawings and the embodiments of the present application are jointly used to explain the present application and do not constitute a limitation to the present application. Unless otherwise specified, in the accompanying drawings, a same symbols and number generally represents a same step or component.

DETAILED DESCRIPTION OF THE EMBODIMENTS

Figure 1:
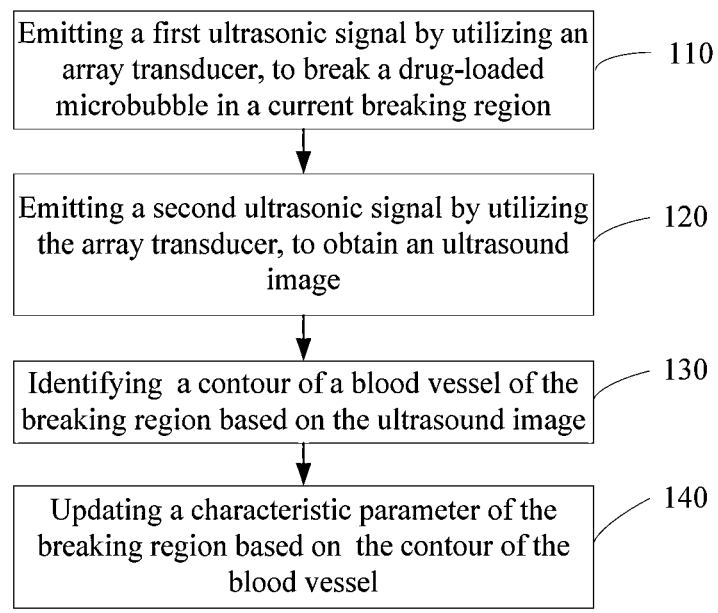
FIG. 1 is a schematic flowchart of a method of delivery of an ultrasound-guided drug-loaded microbubble according to an exemplary embodiment of the present application.

The following clearly and completely describes the technical solutions in the embodiments of the present application with reference to the accompanying drawings in the embodiments of the present application. Apparently, the described embodiments are merely some but not all of the embodiments of the present application. All other embodiments obtained by a person of ordinary skill in the art based on the embodiments of the present application without making creative efforts fall within the protection scope of this application.

Overview

As mentioned above, according to the existing methods of delivery of a drug-loaded microbubble, a focal location for breaking is manually selected through imaging observation of a drug-loaded microbubble, and control and release of drug-loaded microbubbles each time are implemented based on people's experience. Since a location for releasing a drug-loaded microbubble is artificially set, there is a relatively large error. Two array transducers are applied to implement ultrasound imaging and breaking of the drug-loaded microbubble, respectively. The operation of switching between the array transducers is not only complicated to operate, but also affects a response time and accuracy of the location for releasing of the drug-loaded microbubble. Moreover, each release of the drug-loaded microbubbles needs to be manually implemented, which prolongs a delivery time of the drug-loaded microbubbles.

In view of the foregoing problems, the present application provides a method of delivery of an ultrasound-guided drug-loaded microbubble. According to the method, an ultrasonic signal is transmitted toward a drug-loaded microbubble in a current breaking region by utilizing an array transducer to break the drug-loaded microbubble, ultrasound imaging is then implemented by using the array transducer to obtain an ultrasound image, a contour of a blood vessel of the breaking region is obtained based on the ultrasound image, and a characteristic parameter of the breaking region is updated based on the contour of the blood vessel. Since a contour shape of a blood vessel is not static, a parameter of the breaking region is updated in real time to adjust the breaking region, so that the contour of the blood vessel may still be accurately identified when the contour of the blood vessel changes. The delivery accuracy of the drug-loaded microbubble is improved, and a delivery effect of the drug-loaded microbubble is better. In addition, the parameter of the breaking region is continuously updated, so that the breaking region is always kept in the blood vessel, avoiding unnecessary tissue damage caused when an ultrasonic signal is transmitted toward a tissue around the blood vessel, and further shortening a delivery time of the drug-loaded microbubble.

After a basic principle of the present application is introduced, the following describes various non-limiting embodiments of the present application in detail with reference to the accompanying drawings.

Exemplary Method of Delivery of a Drug-loaded Microbubble

FIG. 1 is a schematic flowchart of a method of delivery of an ultrasound-guided drug-loaded microbubble according to an embodiment of the present application. As shown in FIG. 1, the method of delivery of a drug-loaded microbubble includes the following steps.

Step 110: Emitting a first ultrasonic signal by utilizing an array transducer, to break a drug-loaded microbubble in a current breaking region.

The array transducer is an array formed by arranging a plurality of transducers in a specific form, for example, arranged in a linear array, a phased array, or the like. Each transducer, referred to as an array element or an element, is an apparatus that may convert electrical energy and sound energy into each other. The array transducer may transmit an ultrasonic wave or receive a reflected echo. It should be noted that, the array transducer needs to transmit only the first ultrasonic signal when breaking the drug-loaded microbubble, while in the following ultrasound imaging, a second ultrasonic signal needs to be transmitted, and a reflected echo of the second ultrasonic signal also needs to be received and converted into electrical energy for ultrasound imaging on an ultrasound imaging display.

The first ultrasonic signal refers to an ultrasonic beam emitted by the array transducer. Similarly, the following second ultrasonic signal also refers to an ultrasonic beam. The breaking region refers to a location where the ultrasonic beam of the first ultrasonic signal is focused. Specifically, the ultrasonic beam of the first ultrasonic signal is focused in the breaking region to break the drug-loaded microbubble, so as to achieve an effect of drug release.

It should be noted that, the drug-loaded microbubble refers to a microbubble in which a drug may be carried, and the drug carried by the microbubble may be any compound having a therapeutic or prophylactic effect. The compound may be a compound that affects or participates in tissue growth, cell growth, or cell differentiation; or a compound that can cause a biological effect such as an immune response, for example, a compound that inhibits growth of a cancer cell, or a compound that can play any other role in one or more biological processes, which is not specifically limited herein.

The drug-loaded microbubble is usually injected intravenously, or may be injected in another way, for example, injected into a body cavity, an artery, or a lymphatic system. Since the drug-loaded microbubble must be intravenously injectable and small enough to pass through capillaries of most tissues, the drug-loaded microbubble herein ranges from 0.5 microns to 5 microns in diameter. The drug may be carried in a manner of being wrapped in the microbubble or attached to a surface of the microbubble, which is not specifically limited herein. In addition, the drug-loaded microbubble of the present application has a developing function, that is, no additional microbubble contrast agent is required during the following ultrasound imaging.

Step 120: Emitting a second ultrasonic signal by utilizing the array transducer, to obtain an ultrasound image.

Specifically, the ultrasound image obtained by utilizing the second ultrasonic signal emitted by the array transducer is used to monitor a specific situation of the drug-loaded microbubble after the drug-loaded microbubble releases in the breaking region, for example, a concentration of remaining drug-loaded microbubble. It may be determined, whether to continue to break a drug-loaded microbubble and determine a location of a breaking region, based on the specific situation of monitoring the drug-loaded microbubble after the drug-loaded microbubble releases in the breaking region. Thereinto, one or more frames of ultrasound images are obtained by utilizing the second ultrasonic signal emitted by the array transducer, and a specific quantity of ultrasound images obtained is not limited in the present application.

The array transducer of the present application emits the first ultrasonic signal for breaking the drug-loaded microbubble, and also transmits the second ultrasonic signal for generating the ultrasound image. The two ultrasonic signals are alternately emitted, so that both functions of breaking of the drug-loaded microbubble and ultrasound imaging may be implemented. For example, an alternating pulse with a period of 1 ms is used to implement ultrasound imaging and ultrasonic breaking of the drug-loaded microbubble. A same array transducer is used to implement both functions of ultrasound imaging and breaking of the drug-loaded microbubble, and a pulse period is short, that is, a switching speed of the first ultrasonic signal for breaking the drug-loaded microbubble and the second ultrasonic signal for ultrasound imaging is fast. Therefore, controllability of a delivery time and a delivery location of the drug-loaded microbubble is stronger. In addition, due to the short pulse period, an interval time for the array transducer to emit the first ultrasonic signal is short, that is, the interval time for breaking the drug-loaded microbubble is short, making a drug-loaded microbubble dose more controllable, that is, improving controllability of targeted drug delivery.

The ultrasound image in the present application may be a two-dimensional ultrasound image or a three-dimensional ultrasound image, which is not specifically limited herein.

Step 130: Identifying a contour of a blood vessel of the breaking region based on the ultrasound image.

The contour of the blood vessel includes a shape, a size, and the like of a blood vessel. After the drug-loaded microbubble is broken, by monitoring the ultrasound image obtained after the drug-loaded microbubble releases to identify a contour of a blood vessel in real time, so as to prepare for a subsequent parameter adjustment of the breaking region.

Step 140: Updating a characteristic parameter of the breaking region based on the contour of the blood vessel.

Due to movement of an internal organ (such as heartbeat and respiration), there may be a slight change in the contour of the blood vessel before and after the drug-loaded microbubble is broken. Therefore, it is necessary to update the characteristic parameter of the breaking region based on the contour of the blood vessel, to determine a breaking region where a drug-loaded microbubble is to be broken next time, so as to improve breaking accuracy of drug-loaded microbubbles, thereby improving a delivery effect of the drug-loaded microbubbles. In addition, the parameter of the breaking region is continuously updated, so that the breaking region is always kept in the blood vessel, avoiding unnecessary tissue damage caused when an ultrasonic signal is transmitted toward a tissue around the blood vessel.

It should be noted that, in the method of delivery of a drug-loaded microbubble of the present application, a next breaking region may be determined based on an updated characteristic parameter of the breaking region. Characteristic parameters of a breaking region may include a location of the breaking region, a size of the breaking region, a quantity of breaking regions, a shape of the breaking region, and the like.

In another embodiment of the present application, the step of updating a characteristic parameter of the breaking region based on the contour of the blood vessel includes: updating a size and a location of the breaking region based on the contour of the blood vessel.

It should be noted that, a multi-focal manner is adopted to take a release of a drug-loaded microbubble in the present application, so that the breaking region of the present application is in a circular shape or in an oval shape. For example, a diameter of the breaking region is a value between 10% and 90% of the diameter of a current blood vessel, and the center of the breaking region is at the center of the blood vessel. In this case, only after the size and location of the breaking region are updated based on the contour of the blood vessel, the next breaking region may be determined.

It can be learned that, according to the method of delivery of an ultrasound-guided drug-loaded microbubble and apparatus thereof, the electronic device, and the computer-readable storage medium provided in the embodiments of the present application, an ultrasonic signal is transmitted toward a drug-loaded microbubble in a current breaking region by utilizing an array transducer to break the drug-loaded microbubble, then ultrasound imaging is implemented by using the array transducer to obtain an ultrasound image, a contour of a blood vessel of the breaking region is obtained based on the ultrasound image, and a characteristic parameter of the breaking region is updated based on the contour of the blood vessel, to complete delivery of a drug-loaded microbubble of one period. Since a contour and a shape of a blood vessel constantly change, a parameter of a breaking region is updated in real time to adjust the breaking region, so that the contour of the blood vessel may still be accurately identified even the contour of the blood vessel changes, thereby improving delivery accuracy of a drug-loaded microbubble, and making a delivery effect of the drug-loaded microbubble better. In addition, the parameter of the breaking region is constantly adjusted, so that the breaking region is always kept in the blood vessel, thereby avoiding unnecessary tissue damage caused when an ultrasonic signal is transmitted toward a tissue around the blood vessel, and further shortening a delivery time of the drug-loaded microbubble.

Figure 2:
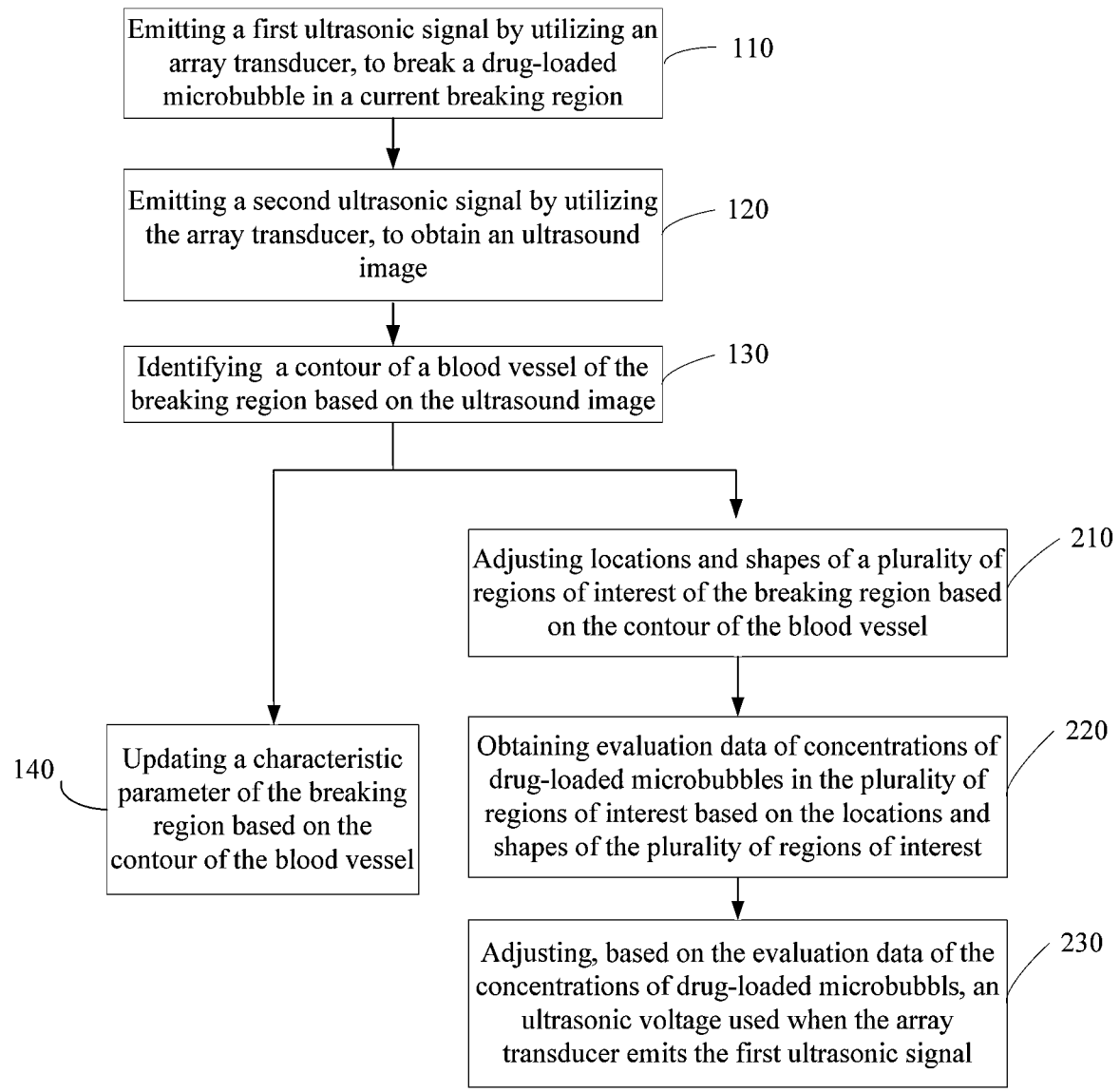
FIG. 2 is a schematic flowchart of a method of delivery of an ultrasound-guided drug-loaded microbubble according to another exemplary embodiment of the present application.

FIG. 2 is a schematic flowchart of a method of delivery of an ultrasound-guided drug-loaded microbubble according to another exemplary embodiment of the present application. The embodiment illustrated in FIG. 2 of the present application is further obtained based on the embodiment illustrated in FIG. 1 of the present application. The following focuses on the differences between the embodiment illustrated in FIG. 2 and the embodiment illustrated in FIG. 1, and the similarities are not repeated.

As shown in FIG. 2, after the step of identifying a contour of a blood vessel of the breaking region based on the ultrasound image, the method of delivery of an ultrasound-guided drug-loaded microbubble according to the embodiment of the present application further includes the following steps.

Step 210: Adjusting locations and shapes of a plurality of regions of interest of the breaking region based on the contour of the blood vessel.

It should be noted that, the plurality of regions of interest of the breaking region refer to contour of local blood vessels around the breaking region, specifically including locations and shapes of local blood vessels.

As mentioned above, due to movement of an internal organ (such as heartbeat), there may be a slight change in the contour of the blood vessel. Therefore, there may also be slight changes in a plurality of contour of local blood vessels, namely, the plurality of regions of interest, around the breaking region. The plurality of regions of interest around the breaking region may be adjusted in real time based on the contour of the blood vessel obtained through ultrasound imaging. It should be noted that, the following evaluation data of the concentrations of drug-loaded microbubbles is obtained from a regional range of the plurality of the regions of interest, and thus the plurality of regions of interest are actual regions for calculating the concentrations of drug-loaded microbubbles.

Step 220: Obtaining evaluation data of concentrations of drug-loaded microbubbles in the plurality of regions of interest based on the locations and shapes of the plurality of regions of interest.

It should be noted that, the concentrations of drug-loaded microbubbles in the present application provide a basis for determining whether to continue with delivery of a drug-loaded microbubble, and provide a basis for adjusting a parameter of an ultrasonic signal during delivery of the drug-loaded microbubble also. Since blood is flowing, after a drug-loaded microbubble releases in a breaking region, the concentrations of drug-loaded microbubbles in and around the breaking region will vary. In this way, the concentrations of drug-loaded microbubbles in different regions may be obtained by calculating the concentrations of the drug-loaded microbubble in the plurality of regions of interest. That is, a regional range of the concentrations of drug-loaded microbubbles for calculating is determined based on the locations and shapes of the plurality of regions of interest, so as to learn the concentration of drug-loaded microbubbles around the breaking region. Moreover, since the obtained evaluation data is of the concentrations of drug-loaded microbubbles in the plurality of regions of interest, the concentration of drug-loaded microbubbles around the breaking region is determined more objectively and accurately.

Step 230: Adjusting, based on the evaluation data of the concentrations of drug-loaded microbubbles, an ultrasonic voltage used when the array transducer emits the first ultrasonic signal.

For example, when the concentrations of drug-loaded microbubbles around the breaking region is greater than a preset value, the ultrasonic voltage used when the array transducer emits the first ultrasonic signal may be increased to enhance an ultrasonic signal, that is, to enhance a capability to break a drug-loaded microbubble. Therefore, more drug-loaded microbubbles may be broken during drug-loaded microbubble breaking next time, thereby shortening a delivery time of a drug-loaded microbubble in a whole process.

Figure 3:
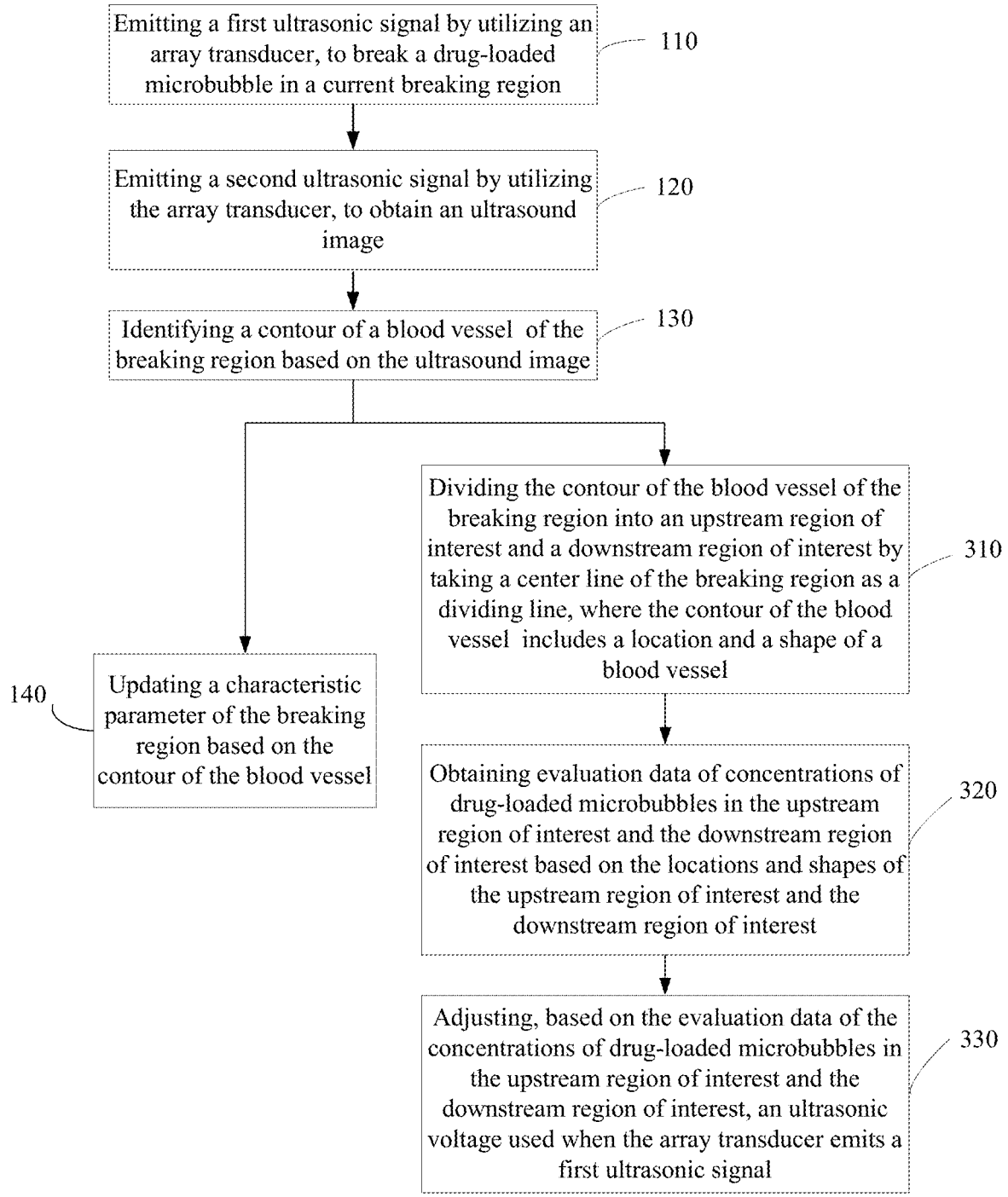
FIG. 3 is a schematic flowchart of a method of delivery of an ultrasound-guided drug-loaded microbubble according to another exemplary embodiment of the present application.

FIG. 3 is a schematic flowchart of a method of delivery of an ultrasound-guided drug-loaded microbubble according to another exemplary embodiment of the present application. The embodiment illustrated in FIG. 3 of the present application is further obtained based on the embodiment illustrated in FIG. 2 of the present application. The following focuses on the differences between the embodiment illustrated in FIG. 3 and the embodiment illustrated in FIG. 2, and the similarities are not repeated.

As shown in FIG. 3, in a method of delivery of an ultrasound-guided drug-loaded microbubble according to an embodiment of the present application, the step of adjusting locations and shapes of a plurality of regions of interest of the breaking region based on the contour of the blood vessel includes the following steps.

Step 310: Dividing the contour of the blood vessel of the breaking region into an upstream region of interest and a downstream region of interest by taking a center line of the breaking region as a dividing line, to learn locations and shapes of the upstream region of interest and the downstream region of interest.

Specifically, in the obtained ultrasound image, a Doppler effect or an inter-frame difference method may be used to determine a blood flow direction of the breaking region. An upstream region along the blood flow direction is determined as the upstream region of interest of the breaking region, and a downstream region along the blood flow direction is determined as the downstream region of interest of the breaking region. In this way, the upstream region of interest and the downstream region of interest of the breaking region are determined. A regional range for obtaining the following evaluation data of the concentrations of drug-loaded microbubbles in the upstream region of interest and the downstream region of interest of the breaking region is delimited. A manner of determining the blood flow direction is not specifically limited in the present application.

Step 320: Obtaining evaluation data of the concentrations of drug-loaded microbubbles in the upstream region of interest and the downstream region of interest based on the locations and shapes of the upstream region of interest and the downstream region of interest.

Specifically, after a drug-loaded microbubble is broken, due to an impact of a blood flow rate, a concentration of drug-loaded microbubbles in the downstream region of interest of the breaking region decreases relative to a concentration of drug-loaded microbubbles in the upstream region of interest. Based on the locations and shapes of the upstream region of interest and the downstream region of interest, a measurement range of the concentrations of drug-loaded microbubbles is determined, and then the evaluation data of the concentrations of drug-loaded microbubbles in the upstream region of interest and the downstream region of interest is obtained.

Based on the evaluation data of the concentrations of drug-loaded microbubbles in the upstream region of interest and the downstream region of interest, changes of the concentrations of drug-loaded microbubbles in the upstream region of interest and the downstream region of interest may be learned, and then used as a basis for adjusting a parameter (such as an ultrasonic voltage) for transmitting the first ultrasonic signal next time, thereby adjusting a condition of breaking drug-loaded microbubble in the breaking region.

Step 330: Adjusting, based on the evaluation data of the concentrations of drug-loaded microbubbles in the upstream region of interest and the downstream region of interest, an ultrasonic voltage used when the array transducer emits a first ultrasonic signal.

A breaking strength of drug-loaded microbubbles is adjusted by adjusting the ultrasonic voltage used when the array transducer emits the first ultrasonic signal, so that the dose of drug-loaded microbubbles is more controllable, that is, controllability of delivery of drug-targeted is improved.

In an embodiment of the present application, the adjusting, based on the evaluation data of the concentrations of drug-loaded microbubbles in the upstream region of interest and the downstream region of interest, an ultrasonic voltage used when the array transducer emits a first ultrasonic signal includes: increasing, based on average gray-scale values of the upstream region of interest and the downstream region of interest, the ultrasonic voltage used when the array transducer emits the first ultrasonic signal.

Specifically, in the ultrasound image, changes of the concentrations of drug-loaded microbubbles in the upstream region of interest and the downstream region of interest may be obtained by calculating the average gray-scale values of the upstream region of interest and the downstream region of interest of the breaking region. The ultrasonic voltage for transmitting the first ultrasonic signal next time toward the breaking region is adjusted, that is, an intensity of the first ultrasonic signal is adjusted, thereby adjusting a breaking strength of drug-loaded microbubbles. When the ultrasonic voltage used when the array transducer emits the first ultrasonic signal is increased, the intensity of the ultrasonic signal is also increased, thereby enhancing a drug-loaded microbubble breaking capability. Therefore, more drug-loaded microbubbles may be broken during drug-loaded microbubble breaking next time, thereby shortening a delivery time of drug-loaded microbubbles in a whole process.

In another embodiment of the present application, the adjusting, based on the evaluation data of the concentrations of drug-loaded microbubbles, an ultrasonic voltage used when the array transducer emits the first ultrasonic signal further includes: when a ratio of an absolute value of a difference between the average gray-scale values of the upstream region of interest and the downstream region of interest to the average gray-scale value of the upstream region of interest is greater than a drug-loaded microbubble breaking threshold, increasing the ultrasonic voltage used when the array transducer emits the first ultrasonic signal.

For example, the ultrasonic voltage is set to increase by 5 V each time, and it should be understood that the ultrasonic voltage in the present application is not infinitely increased. Since different array transducers have different voltage upper limits, different voltage upper limits are set depending on different array transducers in the present application. A voltage upper limit of the array transducer is not specifically limited herein.

In another embodiment of the present application, the identifying a contour of a blood vessel of the breaking region based on the ultrasound image further includes: inputting the ultrasound image into a target tracking model, to obtain the contour of the blood vessel, output by the target tracking model, of the breaking region.

In another embodiment of the present application, the inputting the ultrasound image into a target tracking model, to obtain the contour of the blood vessel, output by the target tracking model, of the breaking region includes: superposing a current ultrasound image and a previous ultrasound image to construct an ultrasound image sequence, and inputting the ultrasound image sequence into the target tracking model, to obtain the contour of the blood vessel, output by the target tracking model, of the breaking region.

Specifically, the target tracking model may use region-based tracking. First, a template including a contour of a blood vessel is obtained, an initialized blood vessel contour around the breaking region is preset, and an algorithm (such as a correlation filtering algorithm) is used to track a target in the ultrasound image sequence, to learn the contour of the blood vessel of the breaking region in real time. For example, first, 50 frames of ultrasound images are obtained through ultrasound imaging to form an ultrasound image sequence, and a box is used to mark a region of interest in the ultrasound image sequence, namely, the initialized blood vessel contour around the breaking region. Then a maximum response filter is obtained through training by utilizing a nuclear correlation filtering method, to ensure that a spatio-temporal convolution of the maximum response filter and the ultrasound image sequence has a maximum value at the location marked by the box, and a model training phase is completed. An ultrasound image is obtained during each ultrasound imaging in a process of identifying the contour of the blood vessel of the breaking region based on the ultrasound image, and a spatio-temporal convolution is performed on the ultrasound image and the maximum response filter. A maximum response location is the location of the region of interest. Thus, a contour of a blood vessel in a current frame of ultrasound image is obtained, and the current frame of ultrasound image in which the contour of the blood vessel is marked is added to the ultrasound image sequence to update the ultrasound image sequence, so that when a contour of a blood vessel is obtained based on a ultrasound image of a subsequent frame, reference can be made to the contour of the blood vessel of the ultrasound image of the current frame, so as to track the contour of the blood vessel in real time.

In another embodiment of the present application, a preselected breaking region is determined as the current breaking region when the array transducer emits the second ultrasonic signal for the first time.

The preselected breaking region may be selected manually, or may be selected by a computer.

As mentioned above, the drug carried by a drug-loaded microbubble may be any compound having a therapeutic or prophylactic effect. In another embodiment of the present application, a drug having a therapeutic effect is carried in a drug-loaded microbubble, and a breaking region may be determined based on a lesion region. When the array transducer emits the first ultrasonic signal for the first time, there is no breaking region in the obtained ultrasound image, and the breaking region of the drug-loaded microbubble is determined by finding the lesion region in the ultrasound image. Therefore, the ultrasound image is obtained when the array transducer emits the second ultrasonic signal for the first time, and the breaking region is selected based on the lesion region in the ultrasound image.

Specifically, for the pre-selected breaking region, a location and a size of the breaking region may be selected by manually observing a location, a size, and the like of a lesion; or a location and a size of the breaking region may be determined based on a location, a size, and the like of a lesion calculated by a computer.

Focus control manners include a single focus control manner, a multi-focus control manner, a variable-focus control manner, and the like. Considering that the breaking region is a region with a specific range, the multi-focus control manner is selected in the present application to implement breaking of drug-loaded microbubbles in the breaking region.

Sizes, locations, and a quantity of basic focal units to be synthesized are determined based on the size and location of the lesion region, and a multi-focus region synthesized by the basic focal units is the breaking region.

In another embodiment of the present application, the selecting the breaking region based on a lesion region in the ultrasound image includes: when the lesion region is a tumor lesion region or a cardiovascular lesion region, determining an upstream region of the lesion region as the breaking region that is selected based on the lesion region in the ultrasound image; when the lesion region is a non-tumor lesion region or a non-cardiovascular lesion region, determining the lesion region as the breaking region that is selected based on the lesion region in the ultrasound image.

Specifically, lesions in the present application are divided into two types: tumor or cardiovascular lesions, and lesions other than tumor or cardiovascular lesions. Different breaking regions are selected in a targeted manner according to different types of lesions, to perform delivery of the drug-loaded microbubble, making delivery of the drug-loaded microbubble more targeted and a therapeutic effect on the lesion region better.

In another embodiment of the present application, ending delivery of current drug-loaded microbubble when a ratio of an absolute value of a difference between average gray-scale values of a current upstream region of interest and an initial upstream region of interest to the average gray-scale value of the initial upstream region of interest is less than a preset value. The average gray-scale value of the initial upstream region of interest is obtained when the array transducer emits the second ultrasonic signal for the first time for obtaining the ultrasound image.

Specifically, the preset value is set to 0.1, and whether to end delivery of current drug-loaded microbubble is determined according to the formula $|V\_up\ t - V\_up\ 1|/(V\_up\ 1 < 0.1)$, where $V\_up\ t$ indicates the average gray-scale value of the upstream region of interest of the current breaking region, and $V\_up\ 1$ indicates the average gray-scale value of the initial upstream region of interest.

In another embodiment of the present application, the array transducer emits the first ultrasonic signal or the second ultrasonic signal under a signal transmission condition that a mechanical index is less than 1.0.

Ultrasound waves with a low mechanical index may reduce damage to ultrasound contrast agent and prolong the life time of ultrasound contrast agent, and also reduce damage to blood vessels of a human body. The mechanical index in the present application is set to be less than 1.5. In some embodiments, the mechanical index may be set to be less than 1.0.

Exemplary Apparatus for Delivery of a Drug-loaded Microbubble

The following describes embodiments of an apparatus for delivery of a drug-loaded microbubble of the present application, which may implement the embodiments of the method of delivery of a drug-loaded microbubble of the present application. For details not disclosed in the apparatus embodiments of the present application, refer to the embodiments of the method of delivery of a drug-loaded microbubble of the present application.

Figure 4:
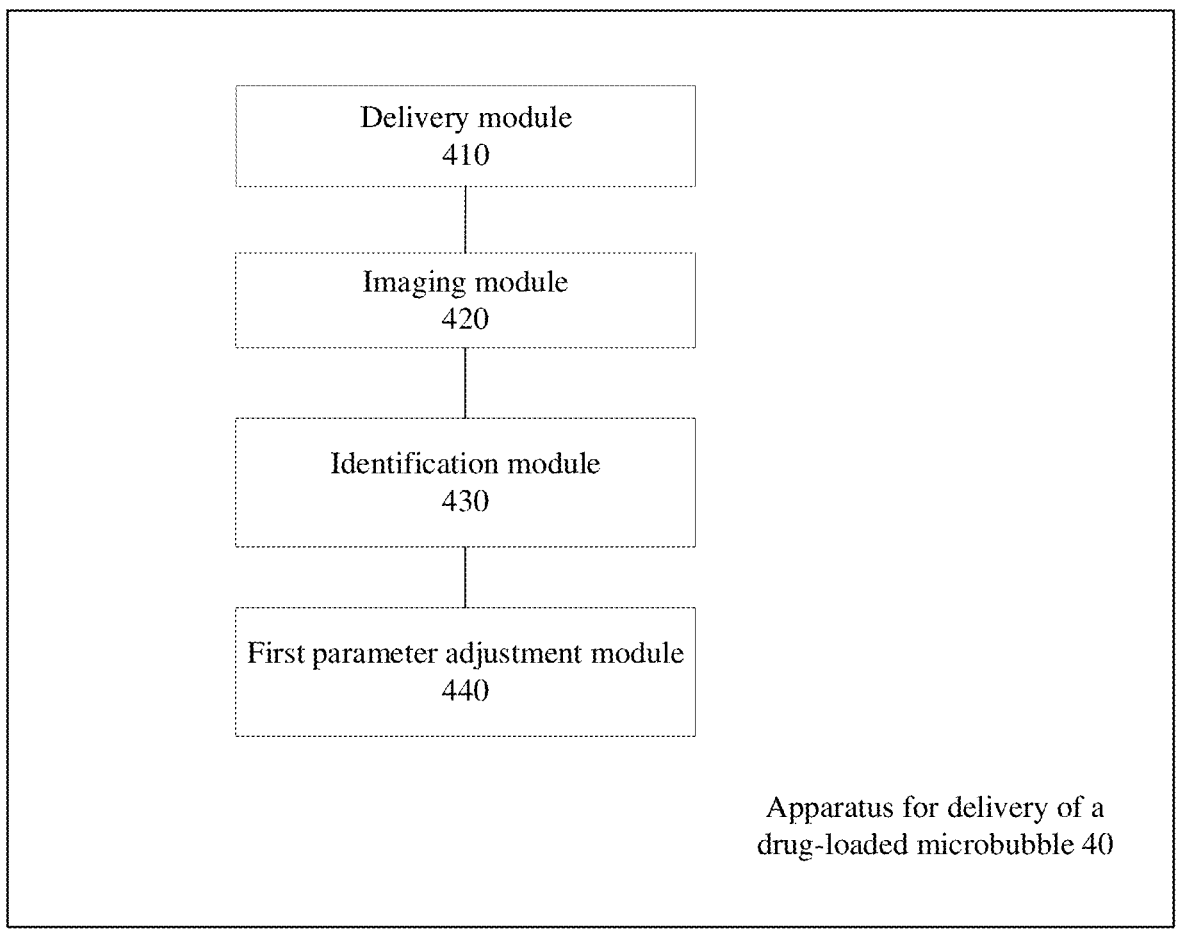
FIG. 4 is a schematic structural diagram of an apparatus for delivery of an ultrasound-guided drug-loaded microbubble according to an exemplary embodiment the present application.

FIG. 4 is a schematic structural diagram of an apparatus for delivery of an ultrasound-guided drug-loaded microbubble 40 according to an embodiment of the present application. As shown in FIG. 4, the apparatus for delivery of a drug-loaded microbubble 40 includes:

a delivery module 410, configured to emit a first ultrasonic signal by utilizing an array transducer, to break a drug-loaded microbubble in a current breaking region;

an imaging module 420, configured to emit a second ultrasonic signal by utilizing the array transducer, to obtain an ultrasound image;

an identification module 430, configured to identify a contour of a blood vessel of the breaking region based on the ultrasound image; and a first parameter adjustment module 440, configured to update a characteristic parameter of the breaking region based on the contour of the blood vessel.

Figure 5:
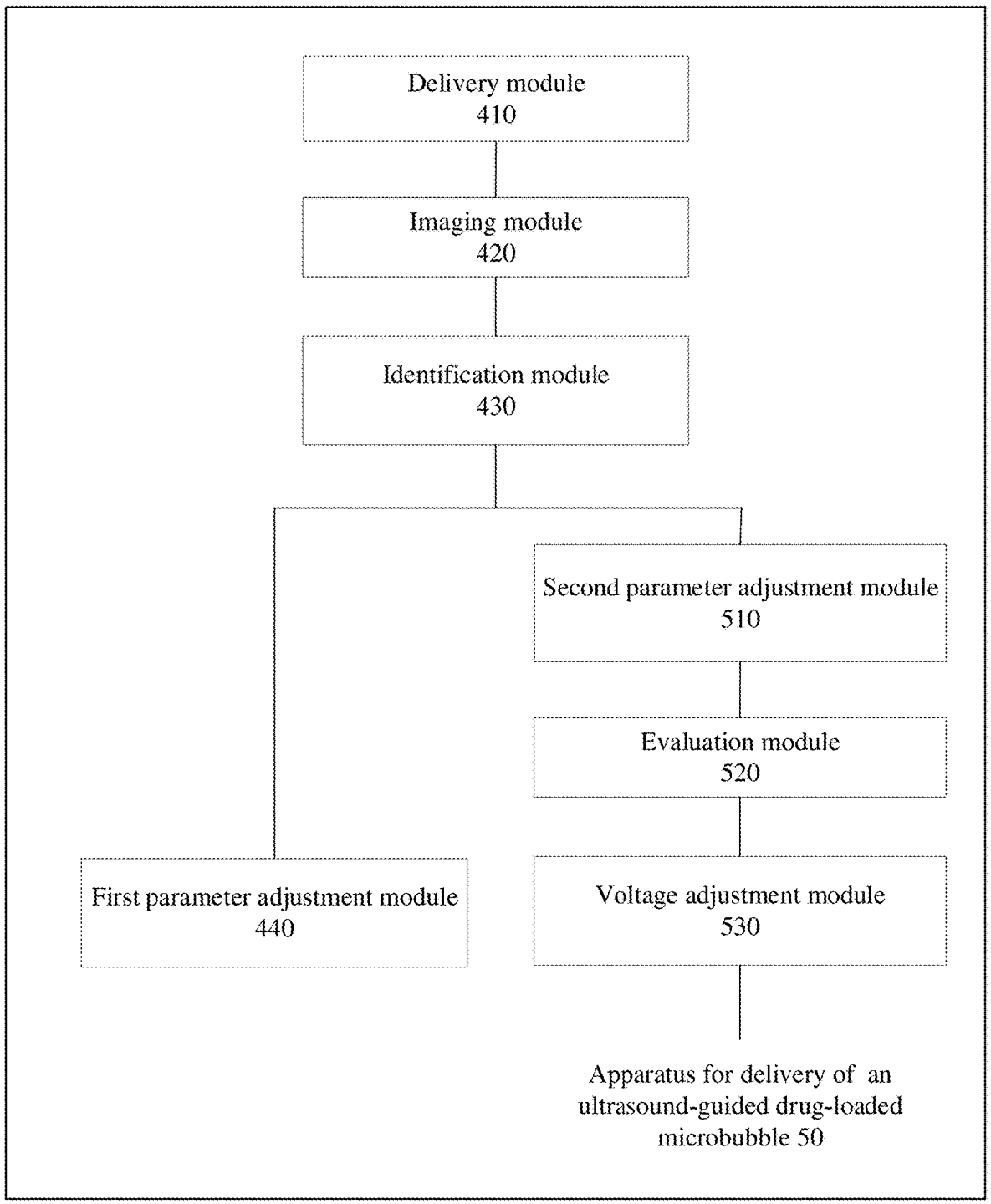
FIG. 5 is a schematic structural diagram of an apparatus for delivery of an ultrasound-guided drug-loaded microbubble according to another exemplary embodiment of the present application.

FIG. 5 is a schematic structural diagram of an apparatus for delivery of an ultrasound-guided drug-loaded microbubble according to another exemplary embodiment of the present application. The embodiment illustrated in FIG. 5 of the present application is further obtained based on the embodiment illustrated in FIG. 4 of the present application. The following focuses on the differences between the embodiment illustrated in FIG. 5 and the embodiment illustrated in FIG. 4, and the similarities are not repeated.

As shown in FIG. 5, an apparatus for delivery of an ultrasound-guided drug-loaded microbubble 50 according to the embodiment of the present application further includes:

a second parameter adjustment module 510, configured to adjust locations and shapes of a plurality of regions of interest of the breaking region based on the contour of the blood vessel;

an evaluation module 520, configured to obtain evaluation data of concentrations of drug-loaded microbubbles in the plurality of regions of interest based on the locations and shapes of the plurality of regions of interest; and a voltage adjustment module 530, configured to adjust, based on the evaluation data of the concentrations of drug-loaded microbubbles, an ultrasonic voltage used when the array transducer emits the first ultrasonic signal.

In another embodiment of the present application, the plurality of regions of interest include an upstream region of interest and a downstream region of interest.

The second parameter adjustment module 510 is further configured to: divide the contour of the blood vessel of the breaking region into the upstream region of interest and the downstream region of interest by taking a center line of the breaking region as a dividing line, to learn locations and shapes of the upstream region of interest and the downstream region of interest.

In another embodiment of the present application, the voltage adjustment module 530 is further configured to: increase, based on average gray-scale values of the upstream region of interest and the downstream region of interest, the ultrasonic voltage used when the array transducer emits the first ultrasonic signal.

In another embodiment of the present application, the voltage adjustment module 530 is further configured to: when a ratio of an absolute value of a difference between the average gray-scale values of the upstream region of interest and the downstream region of interest to the average gray-scale value of the upstream region of interest is greater than a drug-loaded microbubble breaking threshold, increase the ultrasonic voltage used when the array transducer emits the first ultrasonic signal.

In another embodiment of the present application, the identification module 430 is further configured to: input the ultrasound image into a target tracking model, to obtain the contour of the blood vessel, output by the target tracking model, of the breaking region.

In another embodiment of the present application, the identification module 430 is further configured to: superpose a current ultrasound image and a previous ultrasound image to construct an ultrasound image sequence, and input the ultrasound image sequence into the target tracking model, to obtain the contour of the blood vessel, output by the target tracking model, of the breaking region.

In another embodiment of the present application, the first parameter adjustment module 440 is further configured to: update a size and a location of the breaking region based on the contour of the blood vessel.

Specific functions and operations of the modules in the foregoing apparatus for delivery of an ultrasound-guided drug-loaded microbubble have been described in detail in the foregoing method of delivery of an ultrasound-guided drug-loaded microbubble with reference to FIG. 1 to FIG. 3, and thus repeated description thereof will be omitted.

It should be noted that, the apparatus for delivery of an ultrasound-guided drug-loaded microbubble according to the embodiments of the present application may be integrated into an electronic device as a software module and/or a hardware module. In other words, the electronic device may include the apparatus for delivery of an ultrasound-guided drug-loaded microbubble. For example, the apparatus for delivery of an ultrasound-guided drug-loaded microbubble may be a software module in the operating system of the electronic device, or may be an application developed for delivery of an ultrasound-guided drug-loaded microbubble. Certainly, the apparatus for delivery of an ultrasound-guided drug-loaded microbubble may alternatively be one of many hardware modules of the electronic device.

In another embodiment of the present application, the apparatus for delivery of an ultrasound-guided drug-loaded microbubble may alternatively be a device (for example, a server) separate from the electronic device, and the apparatus for delivery of an ultrasound-guided drug-loaded microbubble may be connected to the electronic device via a wired network and/or a wireless network, and transmit interaction information according to an agreed data format.

Exemplary Validation Experiment

Blood flow rates of an artery, a vein and a capillary in a human body are different. Since drug-loaded microbubbles are used for treatment or prevention at different parts, they may need to be delivered to different blood vessel locations. Therefore, in order to verify that the methods of delivery of a drug-loaded microbubble of the present application are feasible at different blood flow rates, the inventor designed experiments for delivery of drug-loaded microbubbles at four different flow rates. The specific experiments are as follows:

uniform mixing ultrapure water and agar in a mass ratio of 10:1, heating the mixture to the boiling point, and continuing to heat the mixture for 3 minutes to obtain a solution A;

transferring the solution A to four square molds each embedded with a cellulose hose (hereinafter referred to as body membrane lumen) whose outer diameter is 1 mm, and waiting 15 minutes until the solution cools to a room temperature;

sucking drug-loaded microbubbles with a same concentration (106/ml) and an average particle size of 1 micron into a syringe, injecting the drug-loaded microbubble solution into one of the body membrane lumen by utilizing an automatic injection apparatus, and allowing the body membrane lumen to stand to make a flow rate inside the body membrane lumen be 0 ml/h;

then injecting the drug-loaded microbubble solution into the remaining three body membrane lumens at flow rates of 10 ml/h, 100 ml/h and 1000 ml/h, respectively, to obtain drug-loaded microbubbles at four flow rates of 0 ml/h, 10 ml/h, 100 ml/h, and 1000 ml/h; and performing delivery of drug-loaded microbubbles by applying the methods of delivery of a drug-loaded microbubble of the present application.

Figure 6:
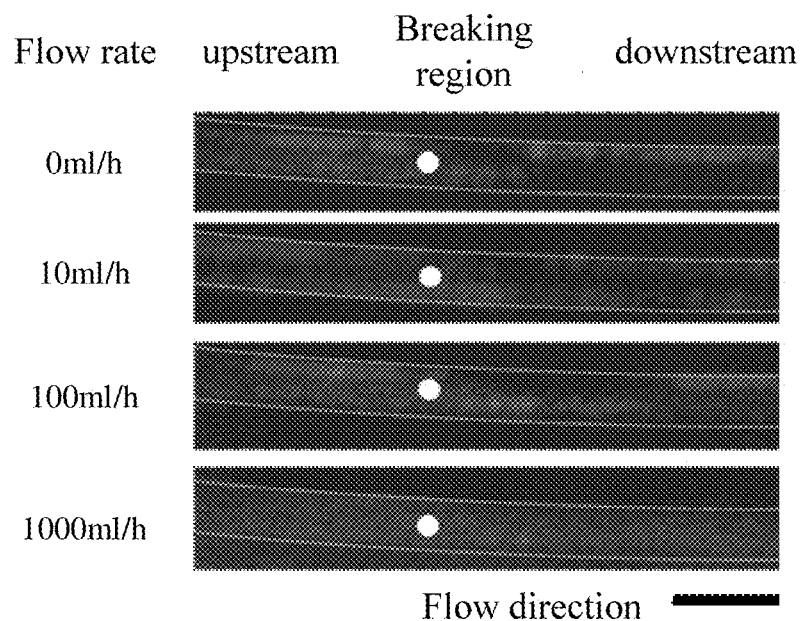
FIG. 6 shows an ultrasound image of delivery of a drug-loaded microbubble at different flow velocities according to an exemplary embodiment of the present application.

FIG. 6 shows ultrasound images of delivery of a drug-loaded microbubble at different flow rates. Delivery of drug-loaded microbubbles may be implemented at different flow rates by applying the methods of the present application. At different flow rates, grayscale of drug-loaded microbubbles in the body membrane lumens shows that concentrations of drug-loaded microbubbles are larger in the upstream region, while the downstream region of the focus region has a lower concentration because the drug-loaded microbubbles are broken in the focus region. It also shows that a real-time concentration of drug-loaded microbubbles may be effectively reflected by using the method of average gray-scale value.

To verify that delivery of drug-loaded microbubbles may indeed be performed in a living body according to the methods of delivery of a drug-loaded microbubble of the present application, the inventor designed a live experiment on a white rabbit. The specific experiment is as follows:

Selecting a white rabbit, performing bolus injection of drug-loaded microbubbles (0.1 ml/kg) with an average particle size of 1 micron on an ear vein of the white rabbit, and waiting 10 seconds until the drug-loaded microbubbles circulate throughout the body.

Placing an ultrasonic linear array probe with a center frequency of 12 MHz on the right waist of the white rabbit vertically, moving the probe until a complete kidney angiography image is observed, and fixing the probe after a proper section is found.

Setting initialization parameters as follows: a focus diameter is set to 1 mm, a voltage U is set to 20 V, an ultrasonic mechanical index MI is set to 1.2, a period is set to 1 ms, and a microbubble breaking threshold Tv is set to 0.5; manually marking an initial location of the breaking region and a blood flow direction at the breaking region (an inter-frame difference method or an ultrasound Doppler may alternatively be used); identifying an upstream region of interest and a downstream region of interest of the breaking region through a target tracking model, so that the diameter of the breaking region is kept at ¾ of a diameter of a blood vessel, and the center of the breaking region is at the center of the blood vessel; and calculating average gray-scale values of an initial upstream region of interest and an initial downstream region of interest.

Figure 7:
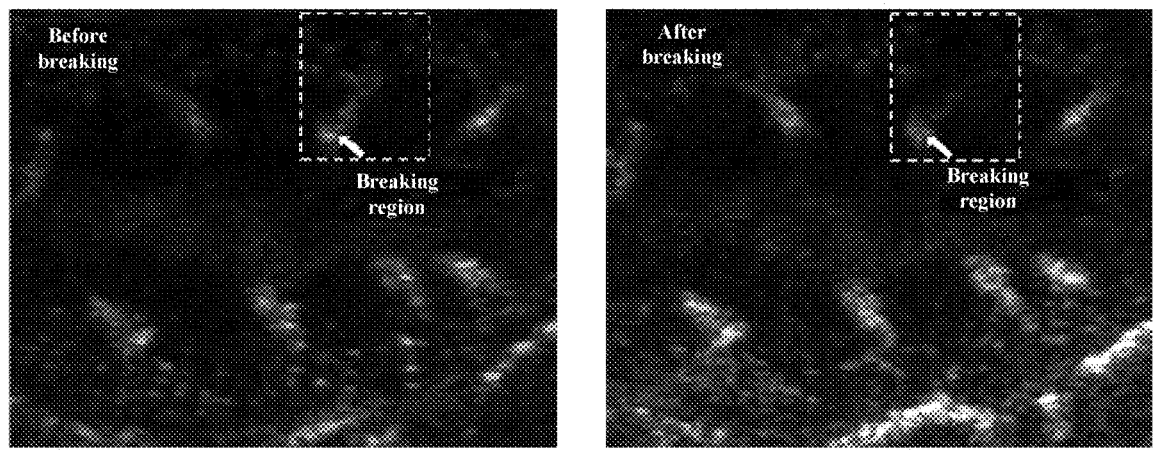
FIG. 7 shows an ultrasound image of delivery of a drug-loaded microbubble in the kidney of a white rabbit according to an exemplary embodiment of the present application.

Periodically applying an alternating pulse sequence to break the drug-loaded microbubbles and implement ultrasound imaging; and obtaining contrast ultrasound images before and after the delivery of the drug-loaded microbubbles in the kidney of the white rabbit, as shown in FIG. 7, where the marked region is the breaking region. It can be seen from the breaking region shown in the figure that, precise delivery of a drug-loaded microbubble may be implemented by applying the methods of the present application.

Exemplary Electronic Device

Figure 8:
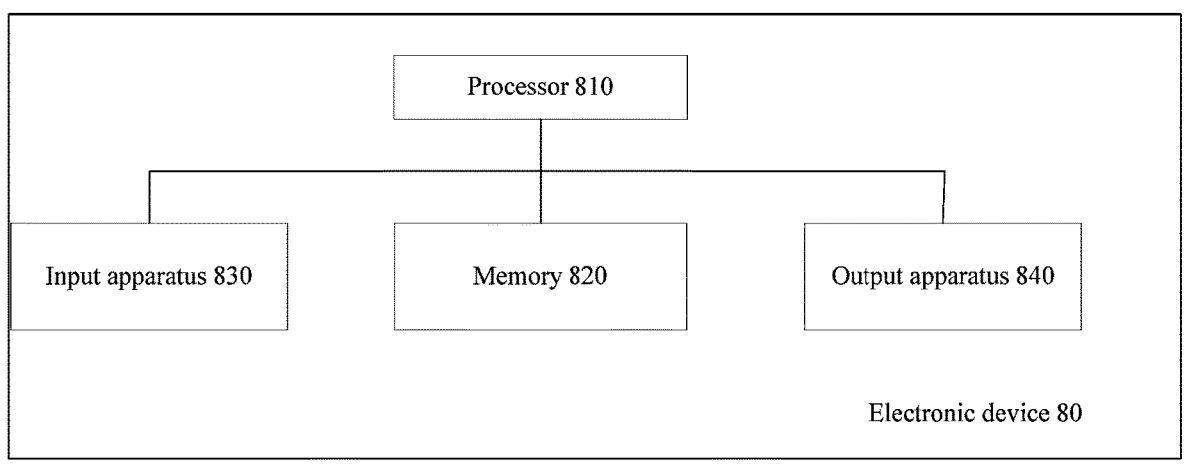
FIG. 8 is a schematic structural diagram of an electronic device according to an exemplary embodiment of the present application.

FIG. 8 is a schematic structural diagram of an electronic device 80 according to another exemplary embodiment of the present application. As shown in FIG. 8, the electronic device 80 includes: one or more processors 810; a memory 820; and computer program instructions stored in the memory 820. When the one or more processors 810 execute one or more computer program instructions, the method of delivery of an ultrasound-guided drug-loaded microbubble according to any one of the foregoing embodiments is implemented.

The processor 810 may be a Central Processing Unit (CPU) or a processing unit in another form that has a data handling capacity and/or instruction execution capacity, and may control another component in the electronic device 80 to perform a desired function.

The memory 820 may include one or more computer program products. The computer program product may include computer-readable storage media in various forms, for example, a volatile memory and/or a nonvolatile memory. The volatile memory may include, for example, a Random Access Memory (RAM) and/or a cache memory (Cache). The nonvolatile memory may include, for example, a Read-Only Memory (ROM), a hard disk, and a flash memory. The computer-readable storage medium may store one or more computer program instructions. The processor 810 can run the program instructions, to implement steps in the method of delivery of an ultrasound-guided drug-loaded microbubble of the foregoing embodiments in the present application and/or another desired function.

The electronic device 80 may further include an input apparatus 830 and an output apparatus 840. These components may be interconnected to each other by using a bus system and/or a connecting mechanism in another form (not shown in FIG. 8).

For example, when the electronic device 80 is a single unit equipment, the input apparatus 830 may be a communication network connector, configured to receive a collected input signal from an external movable device. In addition, the input apparatus 830 may further include, for example, a keyboard, a mouse, and the like.

The output apparatus 840 may output various information to an external device. For example, the external device may include, for example, a display, a printer, a communication network and a remote output device connected thereto.

Certainly, for simplicity, FIG. 8 only shows some of components in the electronic device 80 that are related to the present application, and does not show components such as a bus, an input apparatus/an output interface, and the like. In addition, according to a specific application situation, the electronic device 80 may further include another proper component.

Exemplary Computer-Readable Storage Medium

In addition to the foregoing methods and devices, an embodiment of the present application may alternatively be a computer program product. The computer program product includes computer program instructions. When the computer program instructions are run by a processor, the processor performs steps in the method of delivery of an ultrasound-guided drug-loaded microbubble according to any one of the foregoing embodiments.

The computer program product may use any combination of one or more programming languages to write a program code for performing operations in the embodiments of the present application. The programming languages include an object oriented programming language such as Java, and C++, and further include a conventional procedural programming language, such as the "C" language or a similar programming language. The program code may be entirely executed on a user's computing device, partially on a user's computing device, executed as an independent software package, partially executed on a user's computing device and partially executed on a remote computing device, or entirely executed on a remote computing device or a server.

In addition, an embodiment of the present application may further provide a computer-readable storage medium. The computer-readable storage medium stores a computer program. When the computer program is executed by a processor, the method of delivery of an ultrasound-guided drug-loaded microbubble according to any one of the foregoing embodiments is implemented. The computer-readable storage medium may use any combination of one or more readable media. The readable medium may be a readable signal medium or readable storage medium. The readable storage medium may include, for example, but is not limited to, an electronic, magnetic, electromagnetic, or semiconductor system, apparatus, or means, or any combination thereof. More specific examples (a non-exhaustive list) of the readable storage medium include: an electrical connection having one or more wires, a portable disk, a hard disk, a random access memory (RAM), a read-only memory (ROM), an erasable programmable read-only memory (EPROM or a flash memory), an optical fiber, a portable compact disk read only memory (CD-ROM), an optical storage means, a magnetic storage means, or any suitable combination thereof.

The schematic structural diagrams of means, apparatuses, devices, and systems related in the present application are only examples for illustrative purposes, and are not intended to require or imply that these means, apparatuses, devices, and systems must be connected, arranged, and configured in the manners shown in the schematic structural diagrams. As those skilled in the art will recognize that, these means, apparatuses, devices, and systems may be connected, arranged, and configured in any manner. Words such as "including", "comprising", and "having" are open words, which refer to "including but not limited to" and can be used interchangeably with it. The words "or" and "and" used herein refer to the word "and/or", and can be used interchangeably with it, unless the context clearly indicates otherwise. The word "for example" used herein refer to the phrase "for example, but not limited to", and can be used interchangeably with it. It should be understood that, the terms "first", "second", and the like used in the embodiments of the present application are merely for clear description of the technical solutions of the embodiments of the present application, rather than limiting the protection scope of the present application.

In the embodiments provided in the present application, it should be understood that the disclosed methods and apparatuses may be implemented in other manners. For example, the described apparatus embodiments are merely an example. For example, the module division is merely a logical function division, and there may be other division manners in actual implementation.

In addition, it should be further noted that, a combination form of the technical features in the present application is not limited to the combinations described in the claims of the present application or the combinations described in specific embodiments of the present application. All the technical features described in the present application can be freely combined in any suitable form if such combination is not contradictory.

It should be noted that, the foregoing descriptions are only specific embodiments of the present application. Apparently, the present application is not limited to the foregoing embodiments, and there are various similar variations. All modifications directly derived or conceived by a person skilled in the art from the content disclosed in the present application should fall within the protection scope of the present application.

The foregoing descriptions are merely preferred embodiments of the present application and not intended to limit the present application. Any modifications, equivalent replacements or the like made without departing from the spirit and principle of the present application shall be included within the protection scope of the present application.

The foregoing descriptions are merely preferred embodiments of the present application and not intended to limit the present application. Any modifications, equivalent replacements or the like made without departing from the spirit and principle of the present application shall be included within the protection scope of the present application.

What is claimed is:

1. A method of delivery of an ultrasound-guided drug-loaded microbubble, comprising:
    emitting a first ultrasonic signal to a breaking region of a patient by utilizing an array transducer, to break a drug-loaded microbubble in the breaking region, wherein the drug-loaded microbubble is one or more of a plurality of drug-loaded microbubbles introduced to the patient;
    emitting a second ultrasonic signal by utilizing the array transducer, to obtain an ultrasound image of a region including the breaking region;
    identifying, by a processor, a contour of a blood vessel in the ultrasound image;
    determining, by the processor, that the breaking region is at least partially outside the blood vessel based on the contour of the blood vessel;
    updating, by the processor, a characteristic parameter of the breaking region based on the contour of the blood vessel to obtain an updated breaking region, wherein the updated breaking region is within the blood vessel; and
    controlling, by the processor, the array transducer to emit the first ultrasonic signal to the updated breaking region.

2. The method according to claim 1, after the identifying, by the processor, the contour of the blood vessel in the ultrasound image, further comprising: adjusting locations and shapes of a plurality of regions of interest of the breaking region based on the contour of the blood vessel; obtaining evaluation data of concentrations of drug-loaded microbubbles in the plurality of regions of interest based on the locations and shapes of the plurality of regions of interest; and adjusting, based on the evaluation data of the concentrations of drug-loaded microbubbles, an ultrasonic voltage used when the array transducer emits the first ultrasonic signal.

3. The method according to claim 2, wherein the plurality of regions of interest comprise an upstream region of interest and a downstream region of interest, and the adjusting locations and shapes of a plurality of regions of interest of the breaking region based on the contour of the blood vessel comprises:
    dividing the contour of the blood vessel of the breaking region into the upstream region of interest and the downstream region of interest by taking a center line of the breaking region as a dividing line, to learn locations and shapes of the upstream region of interest and the downstream region of interest.

4. The method according to claim 3, wherein the adjusting, based on the evaluation data of the concentrations of drug-loaded microbubbles, the ultrasonic voltage used when the array transducer emits the first ultrasonic signal comprises: increasing, based on average gray-scale values of the upstream region of interest and the downstream region of interest, the ultrasonic voltage used when the array transducer emits the first ultrasonic signal.

5. The method according to claim 4, wherein the increasing, based on average gray-scale values of the upstream region of interest and the downstream region of interest, the ultrasonic voltage used when the array transducer emits the first ultrasonic signal comprises:
    when a ratio of an absolute value of a difference between the average gray-scale values of the upstream region of interest and the downstream region of interest to the average gray-scale value of the upstream region of interest is greater than a drug-loaded microbubble breaking threshold, increasing the ultrasonic voltage used when the array transducer emits the first ultrasonic signal.

6. The method according to claim 1, wherein the identifying, by the processor, the contour of the blood vessel in the ultrasound image comprises: inputting the ultrasound image into a target tracking model, to obtain the contour of the blood vessel, output by the target tracking model, of the breaking region.

7. The method according to claim 6, wherein the inputting the ultrasound image into the target tracking model, to obtain the contour of the blood vessel, output by the target tracking model, of the breaking region comprises: superposing a current ultrasound image and a previous ultrasound image to construct an ultrasound image sequence, and inputting the ultrasound image sequence into the target tracking model, to obtain the contour of the blood vessel, output by the target tracking model, of the breaking region.

8. The method according to claim 1, wherein the updating, by the processor, the characteristic parameter of the breaking region based on the contour of the blood vessel comprises:

updating a size and a location of the breaking region based on the contour of the blood vessel.

9. The method according to claim 1, wherein a preselected breaking region is determined as the current breaking region when the array transducer emits the second ultrasonic signal for the first time.

10. The method according to claim 9, wherein the determining the preselected breaking region as the current breaking region when the array transducer emits the second ultrasonic signal for the first time comprises: obtaining the ultrasound image when the array transducer emits the second ultrasonic signal for the first time, and selecting the breaking region based on the lesion region in the ultrasound image.

11. The method according to claim 10, wherein the selecting the breaking region based on the lesion region in the ultrasound image comprises: when the lesion region is a tumor lesion region or a cardiovascular lesion region, determining the upstream region of the lesion region as the breaking region that is selected based on the lesion region in the ultrasound image; and when the lesion region is a non-tumor lesion region or a non-cardiovascular lesion region, determining the lesion region as the breaking region that is selected based on the lesion region in the ultrasound image.

12. The method according to claim 5, further comprising: ending delivery of current drug-loaded microbubble when the ratio of the absolute value of the difference between average gray-scale values of a current upstream region of interest and the initial upstream region of interest to the average gray-scale value of the initial upstream region of interest is less than a preset value, wherein the average gray-scale value of the initial upstream region of interest is obtained when the array transducer emits the second ultrasonic signal for the first time for obtaining the ultrasound image.

13. The method according to claim 1, wherein the array transducer emits the first ultrasonic signal or the second ultrasonic signal under a signal sending condition that a mechanical index is less than 1.0 or 1.5.

14. The method according to claim 1, wherein the breaking region is in a circular shape or in an oval shape.

15. The method according to claim 1, wherein the breaking region is in a circular shape, and a diameter of the breaking region is in a range from 10% to 90% of a diameter of the blood vessel.

16. The method according to claim 1, wherein the emitting the first ultrasonic signal to the breaking region of the patient by utilizing the array transducer, to break the drug-loaded microbubble in the breaking region comprises: using a multi-focus control manner, to implement breaking of drug-loaded microbubbles in the breaking region.

17. The method according to claim 1, wherein the first ultrasonic signal and the second ultrasonic signal are alternately emitted by the array transducer.

18. A non-transitory computer-readable storage medium, wherein the storage medium stores a computer program, and when the computer program is executed by a processor, the method of delivery of the ultrasound-guided drug-loaded microbubble according to claim 1 is implemented.

19. An electronic device, comprising:
a processor; and
a memory, wherein the memory is configured to store instructions executable by the processor, wherein when the processor executes the instructions, the method of delivery of the ultrasound-guided drug-loaded microbubble according to claim 1 is implemented.

* * * * *